US005840044A

United States Patent [19]

Dassa et al.

[11] Patent Number: 5,840,044

[45] Date of Patent: Nov. 24, 1998

[54] MULTIPLE BIOPSY SAMPLING FORCEPS

[75] Inventors: Alyssa J. Dassa, Chestnut Hill; Bruce H. Diamond, Brookline, both of Mass.

[73] Assignee: Boston Scientific Corporation, Watertown, Mass.

[21] Appl. No.: 626,918

[22] Filed: Apr. 3, 1996

Related U.S. Application Data

[63] Continuation of Ser. No. 129,653, Sep. 30, 1993, abandoned.

[51] Int. Cl.[6] .......... A61B 5/00

[52] U.S. Cl. .......... 600/567; 606/170

[58] Field of Search .......... 600/562, 564–567; 606/205–207, 167, 170

[56] References Cited

U.S. PATENT DOCUMENTS

| | | | |
|---|---|---|---|
| 2,541,542 | 2/1951 | Perez et al. . | |
| 3,147,749 | 9/1964 | Marsh | 128/751 |
| 3,902,498 | 9/1975 | Niederer . | |
| 3,924,608 | 12/1975 | Mitsui | 128/751 |
| 4,007,732 | 2/1977 | Kvalve et al. | 128/754 |
| 4,220,155 | 9/1980 | Kimberling et al. . | |
| 4,243,048 | 1/1981 | Griffin | 128/754 X |
| 4,651,752 | 3/1987 | Fuerst . | |
| 4,682,606 | 7/1987 | DeCaprio . | |
| 4,708,147 | 11/1987 | Haaga . | |
| 4,712,550 | 12/1987 | Sinnett | 606/170 X |
| 4,785,809 | 11/1988 | Weinrib . | |
| 4,785,826 | 11/1988 | Ward . | |
| 4,817,630 | 4/1989 | Schintgen et al. | 128/751 |
| 4,887,612 | 12/1989 | Esser et al. | 128/749 X |
| 4,936,845 | 6/1990 | Stevens | 606/171 X |
| 4,953,559 | 9/1990 | Salerno | 128/751 |
| 5,082,000 | 1/1992 | Picha et al. . | |
| 5,085,659 | 2/1992 | Rydell . | |
| 5,133,360 | 7/1992 | Spears . | |
| 5,171,255 | 12/1992 | Rydell . | |
| 5,228,451 | 7/1993 | Bales et al. . | |
| 5,242,461 | 9/1993 | Kortenbach et al. | 606/170 X |
| 5,331,971 | 7/1994 | Bales et al. | 128/749 |
| 5,342,390 | 8/1994 | Slater et al. | 128/749 |
| 5,373,854 | 12/1994 | Kolozsi . | |
| 5,375,608 | 12/1994 | Tiefenbrun et al. . | |
| 5,383,471 | 1/1995 | Funnell | 128/751 |
| 5,394,887 | 3/1995 | Haaga | 128/754 |

FOREIGN PATENT DOCUMENTS

| | | | |
|---|---|---|---|
| 0 225 045 | 6/1987 | European Pat. Off. . | |
| 93/04630 | 3/1993 | WIPO | 128/754 |
| WO 94/15533 | 7/1994 | WIPO . | |

OTHER PUBLICATIONS

U.S. Patent Application Serial No. 08/062,671 to Chu et al., filed May 17, 1993.

U.S. Patent Application Serial No. 08/124,272 to Diamond et al., filed Sep. 20, 1993.

*Primary Examiner*—Max Hindenburg
*Attorney, Agent, or Firm*—Finnegan, Henderson, Farabow, Garrett & Dunner, L.L.P.

[57] ABSTRACT

The invention features a device for obtaining tissue samples from a site deep within the body having a proximal portion constructed to follow a long torturous path to the site and a distal portion constructed with a jaw arrangement that can be opened and closed to sever a sample, including tissue specimens, polyps and the like, from the surface. The device is constructed for severing and storing at least three successive samples. The device includes a sample storing and retaining element in the space encompassed by the jaws. The element is fixed to maintain an orientation extending generally distally along a selected length to a distal end and has a profile along the length for engaging multiple samples arranged axially in the order in which they were severed from the surface with sufficient frictional force to substantially retain the samples from moving distally from the space encompassed by the jaws when the jaws are opened to sever a successive sample from the surface.

33 Claims, 5 Drawing Sheets

16 30 32 42 d3 48 36 44 50 41 38 1 2 3 4 46 40 34 θ 30a L4

10
16
18
11

$d_2$ $d_1$

MULTIPLE BIOPSY SAMPLING FORCEPS

This is a continuation of application Ser. No. 08/129,653, filed Sep. 30, 1993, now abandoned.

FIELD OF THE INVENTION

This invention relates to taking samples of tissue from the body for biopsy analysis.

BACKGROUND OF THE INVENTION

Tissue samples can be examined in a laboratory to determine the presence of a pathological disorder (e.g. malignancy). Often, the samples must be obtained from deep within the body using a medical sampling instrument. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In a first aspect, the invention features a device for obtaining tissue samples from a site deep within the body having a proximal portion constructed to follow a long torturous path to the site and a distal portion constructed with a jaw arrangement that can be opened and closed to sever a sample, including tissue specimens, polyps and the like, from the surface. The device is constructed for severing and storing at least three successive samples. The device includes a sample storing and retaining element in the space encompassed by the jaws. The element is fixed to maintain an orientation extending generally distally along a selected length to a distal end and has a profile along the length for engaging multiple samples that are arranged axially in the order in which they were severed from the surface. The element engages samples with sufficient frictional force to substantially retain the samples from moving distally from the space encompassed by the jaws when the jaws are opened to sever a successive sample from the surface.

In another aspect, the invention features a device for obtaining tissue samples having a distal end constructed with a jaw arrangement that can be opened and closed to sever the sample, including tissue specimens, polyps and the like, from a surface. The device is constructed for severing storing at least five successive samples. The device includes an elongated sample storing and retaining element in the form of an elongated spear-form member in the space encompassed by the jaws. The member is fixed to maintain an orientation extending along a selected length to a distal end constructed to pierce the samples and allow proximal sliding of previous samples along its length during piercing of tissue to take a successive sample. The element includes near its distal end a retaining protrusion extending to diameter larger than the diameter of portions proximal of the protrusion. The protrusion provides sufficient frictional force to substantially retain a sample positioned at least in part proximally of the protrusion from moving distally from the space encompassed by the jaws when the jaws are opened to sever a successive sample from the surface. The length of the protrusion is less than about 15% of the length of element.

The features of the aspects above can be combined. Embodiments may include one or more of the following.

The element has a profile of smaller diameters distal of the retaining protrusion to facilitate piercing of the tissue. The protrusion is integral with the tissue-piercing profile. The protrusion and tissue piercing profile are about 5 to 15% of the length of the member proximal of the protrusion. The length of the element proximal of the retaining protrusion is about 0.065 inch or longer. The length of the element proximal of the retaining protrusion is about 0.300 inch. The maximum diameter of the retaining protrusion is about 25–250% larger than portions of the element proximal of the protrusion. The element has a substantially constant diameter proximal of the retaining protrusion. The element has a diameter of about 0.010 inch or larger. The protrusion and the tissue piercing profile form an arrow head-type profile. The sample-retaining element is constructed for deattachment from the device at a location proximal of samples stored on the member. The sample-retaining element and device include mating structure so a sample retaining element can be detached and attached to the device. The sample-retaining element and device include a plug and socket-type mating arrangement. The length and profile are constructed for retaining at least five successive samples. The element is of substantially constant diameter for most of its length and includes textural surface on at least part of its length to substantially retain the sample. The element extends proximally from the larger diameter of the retaining protrusion to smaller diameters along a continuous gradual angular profile. The transition between portions of different diameter are rounded for smooth distal sliding release of the samples after removal from the body.

In another aspect, the invention features a method of taking multiple biopsy samples. The method includes providing a device as described above and delivering the device deep into the body along a torturous path to a desired site. The method also includes opening the jaw arrangement, extending the device distally to imbed the spear-form element into a tissue surface at the desired site, and closing the jaws to sever a sample from the surface. The opening, extending and closing steps are repeated to take additional samples. The device is removed from the body and the samples removed from the device.

In particular aspects, the samples may be recovered from the device by detaching the element. At least five samples may be taken before removing the device from the body.

BRIEF DESCRIPTION OF THE DRAWING

We first briefly describe the drawings.

DESCRIPTION OF THE PREFERRED EMBODIMENTS

Figure 1:
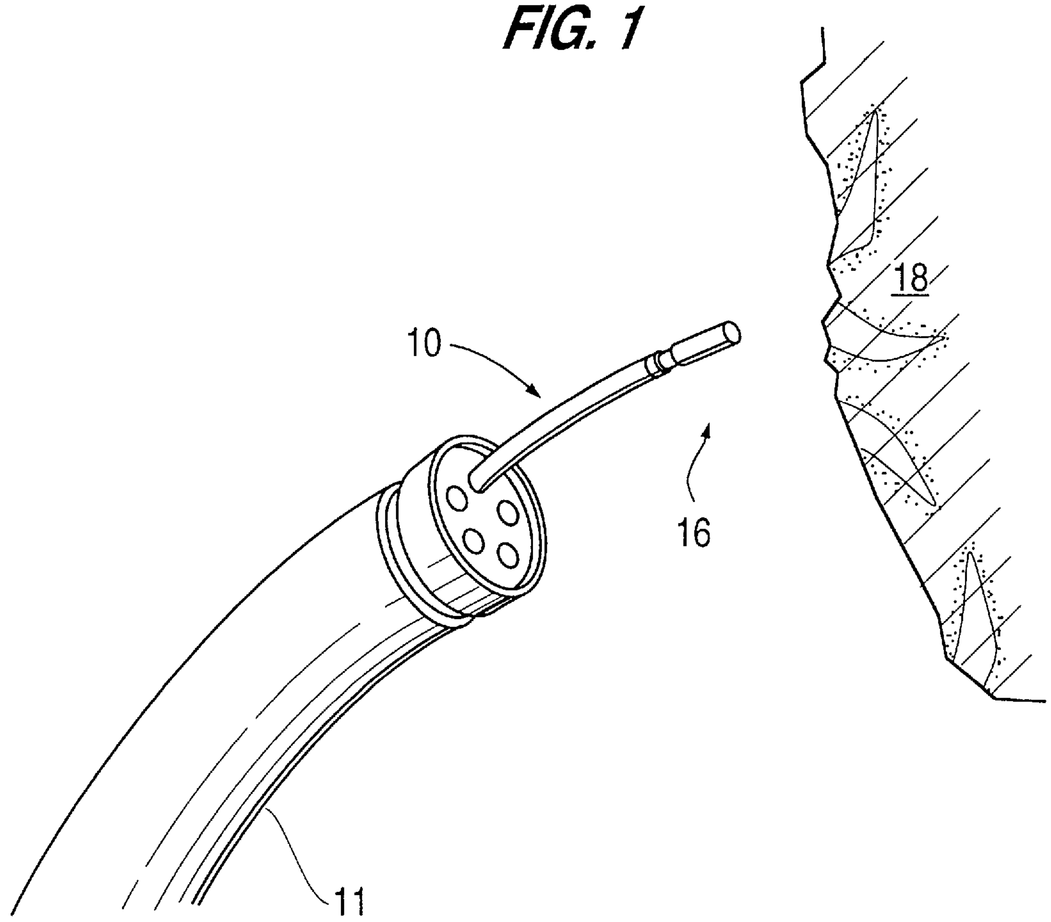
FIG. 1 is a perspective view of an embodiment of the invention being delivered into the body through an endoscope.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g., from a surface in the gastrointestinal tract or bronchial tract). The device has a diameter of preferably around 1.8–2.4 mm, typically about 2.3 mm or less and is of sufficient flexibility so it passes easily though the channel when the endoscope follows a tortuous body passageway. The endoscope includes other lumens for water, air, suction, and viewing. Devices according to the invention can be adapted to be introduced to sites (e.g., urinary tract, reproductive organs, cardiac tissue, or the like) deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications.

Figure 2:
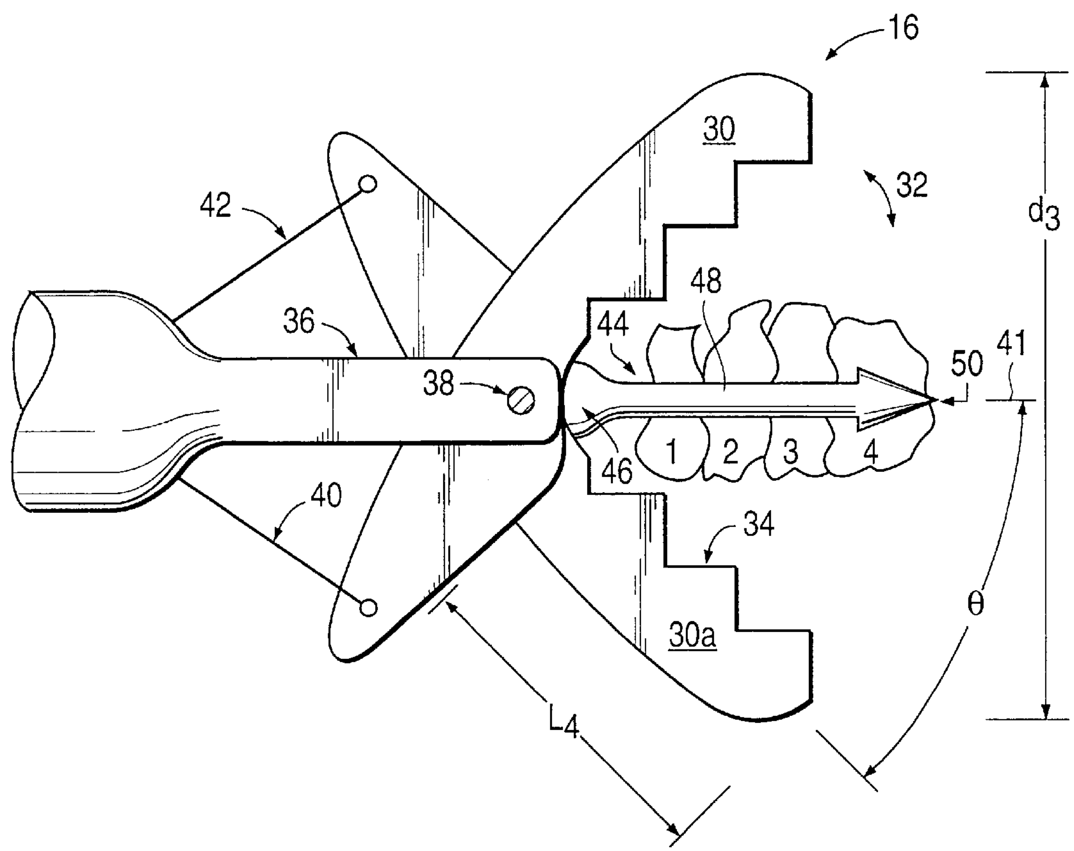
FIGS. 2, 2*a*–2*d* illustrate the structure of an embodiment of the invention.
Figure 2A:
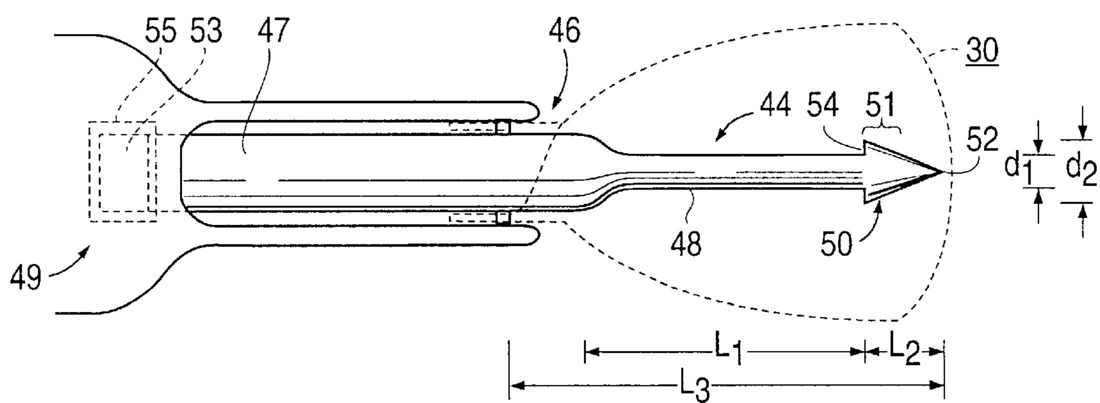
Figures 2B, 2C, 2D:
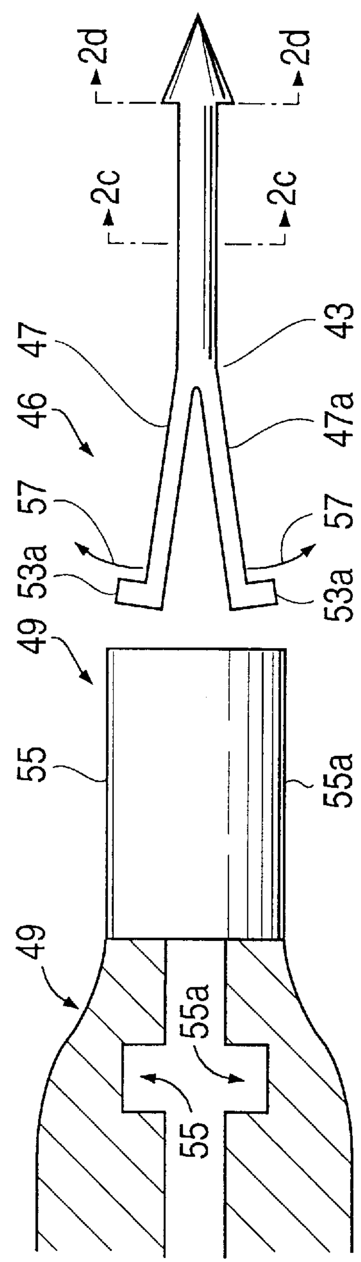

Referring to FIGS. 2–2*d,* particularly FIG. 2, the sampling portion 16 includes a forceps-type device with a pair of jaw members 30, 30*a* which are movable with respect to each other (arrow 32) between an open and closed position. The jaw members may include jagged edges 34 around their periphery for cutting a sample of tissue from a body surface. The jaw members are attached to the distal end of the device body 36 at a pivot pin 38. The opening and closing of the jaw members can be controlled from proximal portions of the device using pull wires 40, 42. The jaw members have a length, $L_4$, coordinated to accommodate a sample storing and retaining member 44, and open to an angle θ, and a width $d_3$. The spear-form sample storing and retaining member 44, formed, e.g., of metal, is positioned within the space encompassed by the jaws and fixed with respect to the body of the device. Sampling retaining member 44 is constructed and oriented for storing multiple samples, at least three, preferably five or more. The jaws may be elongated to accommodate a long member 44 to store a large number of samples.

The retaining member 44 includes a proximal portion 46 for attaching the element to the device, an elongated body 48, for storing, e.g., samples 1–4, and a distal portion 50 shaped like an arrow (shown) or barb that is used to pierce the samples and to help retain them on the element as the jaws are opened in preparation to cut another sample from the tissue surface.

Referring particularly to FIGS. 2*a* and 2*b,* respectively, a top view and a partial cross-sectional side view with the jaws not shown, the proximal portion 46 may include plug members 47, 47*a* which are mateable with a socket arrangement 49 in body 36 of the device. The plug members 47, 47*a* extend around and proximal of the pivot pin 38 to feet 53, 53*a* that lock into cutouts 55, 55*a* in the body 36. The plug members may be biased outward with respect to the spacing of the socket openings (arrows 57, FIG. 2*b*) so the members bear on the inside of the openings to prevent rotation or axial motion of the retaining member 44. After a sufficient number of samples have been taken and the device removed from the body, the plug members can be removed from the socket openings by manually overcomming the bias of the legs 47, 47*a* to remove the feet 53, 53*a* from the cutouts 55, 55*a* and then moving the member 44 axially distally. The member 44, holding the samples, can be sent to the lab where the plug members can be removed e.g. by cutting at a location proximal of the samples, (dotted line 43) and slipping the samples off the body 48. Other attachment assemblies, e.g. screw-forms, indents, etc. can also be used to attach the member to the device. For a single-use forceps instrument, the member 44 can simply be removed by cutting at a region proximal of the samples stored on the body 48.

The length of the member 44 extending distally of the pivot pin is $L_3$. The body portion 48 is of substantially constant diameter, $d_1$, over an extended length, $L_1$, selected to accommodate a desired number of samples. Referring particularly to FIG. 2*c,* the body portion is of substantially narrow, uniform, symmetric cross-sectional dimension.

The distal portion 50 has a protrusion 51 to diameters larger than the diameter, $d_1$, of the body portion proximal of the protrusion. The maximum diameter of the protrusion is $d_2$. The proximal edge 54 of the protrusion extends distally with an abrupt profile. The proximal edge 54 may extend substantially perpendicular to the axis of the body 48. Distally and integrally with the protrusion 51, the portion 50 extends along a gradual conical surface to a sharp tip 52 for piercing tissue. Referring particularly to FIG. 2*d,* the cross-sectional profile of the protrusion and distal portion are narrow and symmetric. The distal portion has a short length, $L_2$. The relatively gradual angle of distal conical surface and the abrupt angle in the distal direction of surface 54 allows the member to pierce tissue, then retain tissue samples from slipping off when the jaws are opened while the device is still in the body.

In embodiments, the maximum diameter, $d_2$, of the protrusion 51 is preferably 25–50% (or more, up to e.g. 250%) larger than the diameter, $d_1$, of the body 48. The portion 50 and protrusion 51 are also relatively short compared to the body 48 so that samples may be disposed proximally of the portion 50 and retained against distal motion. The length, $L_2$, of the distal portion 50 is about 5–15% of the length, $L_1$, of the body 48. The length of the protrusion is less than 15% of the length of the body.

Typical embodiments include the following combinations of dimensions. The body 48 of the member has a length, $L_1$, about 0.065 to 0.300 inch, and a diameter, $d_1$, about 0.010 to 0.035 inch. The distal portion 50 has a length, $L_2$, about 0.015 to 0.035 inch and a maximum diameter $d_2$, about 0.015 to 0.045 inch. The overall length, $L_3$, of the member 44 is about 0.075 to 0.325 inch. The jaw members have a working length of, $L_4$, about 0.101 to 0.350 inch. The jaws open to an angle, θ, e.g. about 450 (may vary) with respect to the axis 41 of the device, creating an opening of diameter, $d_3$, about 0.225 to 0.350 inch. A particular embodiment for taking five successive samples has body length, $L_1$, of about 0.300 inch, a distal portion length, $L_2$, of about 0.015 inch, a body diameter, $d_1$, of 0.010 inch, a distal portion maximum diameter, $d_2$, of about 0.015 inch, and the jaws are elongated to a length, $L_4$, of about 0.350 inch.

Figure 3:
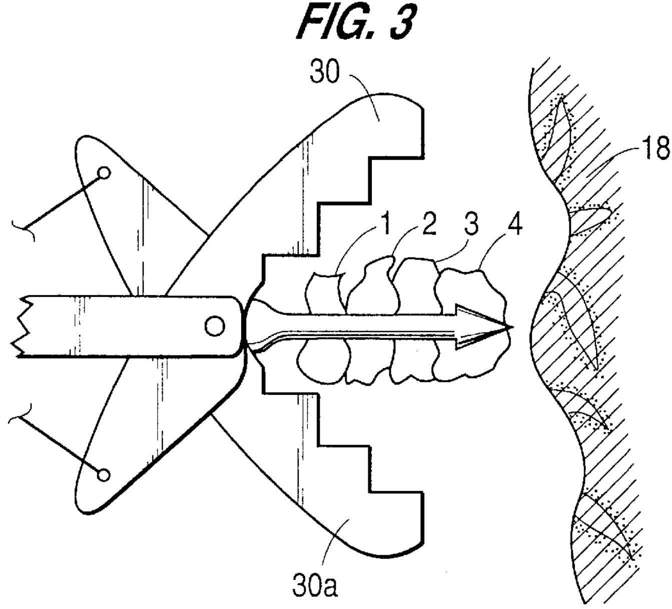
FIGS. 3, 3*a*–3*b* illustrate the use of an embodiment of the invention.
Figure 3A:
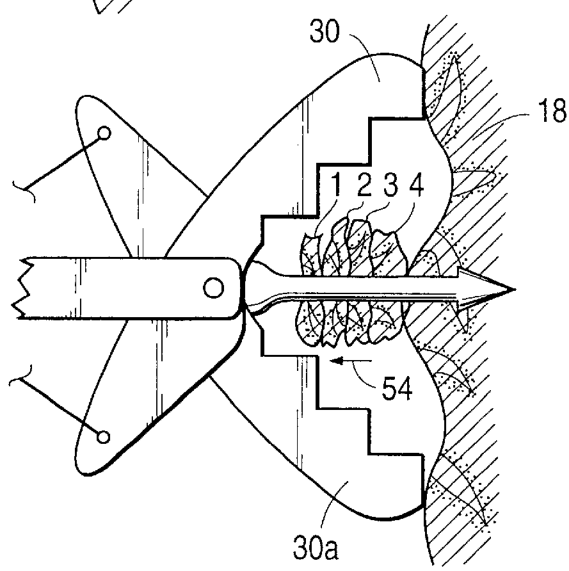

Referring to FIGS. 3–3*a,* particularly FIG. 3, in use, after the device has been delivered into the body, the jaws 30, 30*a* are placed in the open position. The protrusion 51 on the distal portion 50 prevents previously-taken samples 1–4 from slipping distally off the retaining member 44. Referring to FIG. 3*a,* the spear-form retaining member is advanced into a tissue surface 18 at a location where an additional sample is to be taken. As the element 44 is advanced the pressure applied in the distal direction displaces (arrow 54), the previous samples, samples 1–4, distally along the long narrow body 48 of the member 44. The member 44 is advanced distally such that the entire short distal portion, beyond the protrusion 51, is inside tissue.

Figure 3B:
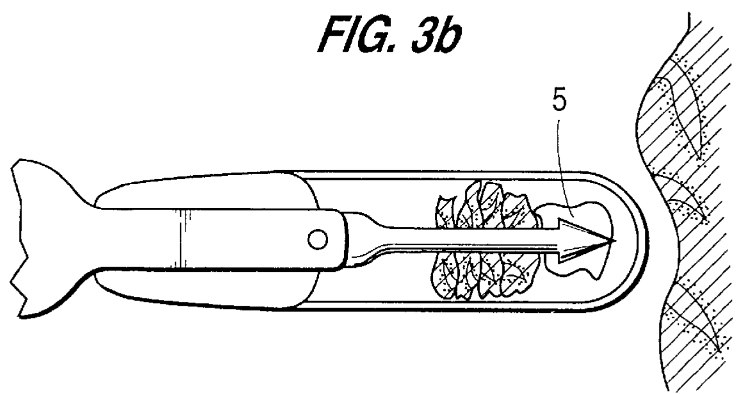

Referring to FIG. 3*b,* the jaws 30, 30*a* are closed and the cutting edge 34 cuts or evulses the next sample, sample 5, from the tissue surface 18. The protrusion 51 holds sample 5 and the other samples axially in place. The device can be removed from the body and the samples recovered for laboratory analysis or, if sufficient retaining element length is provided, the process above can be repeated for taking still additional samples. After a sufficient number of samples have been taken, the device is removed from the body and the sample recovered (e.g. by removing the element 44 as discussed above) and sent to a laboratory for analysis. In cases where structure is provided for reattachment, a new element is installed in the jaws for further sampling.

OTHER EMBODIMENTS

Figure 4:
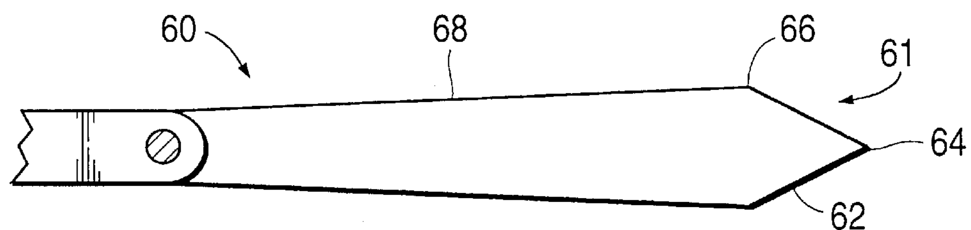
FIGS. 4–8 illustrate additional embodiments of the invention.

Referring to FIG. 4, in another embodiment, a sample retaining member 60 includes a distal portion 61 with an angular surface 62 extending distally to smaller diameters and a sharp tip 64. Proximal of a retaining region 66, the member includes a continuous gradual angular storage surface 68 that extends to smaller diameters in the proximal direction. In this embodiment, the angle of the surface 68 may be more gradual than the angle of surface 62; the profile and length of the surface 68 discourages samples from slipping beyond the retaining region 66 when the jaws are opened in preparation for taking an additional sample.

Figure 5:
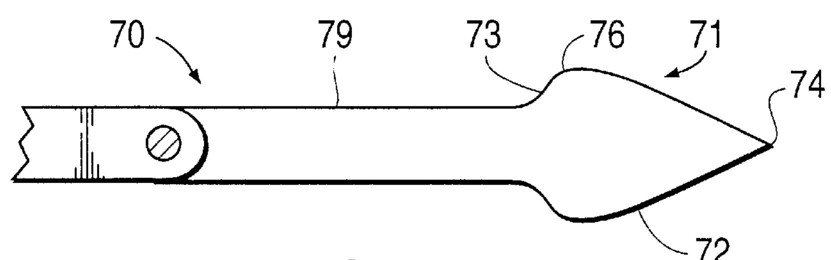

Referring to FIG. 5, a retaining element 70 includes a short distal portion 71 that includes a surface 72 extending distally to smaller diameter, such as to a sharp point 74, and a rounded surface near a retaining region 76. The rounded surface gradually transitions into a relatively abrupt angular surface 78, that extends to a body 79 of substantially constant diameter. The shape and diameter difference between the body 79, transitioning along surface 78 to the region 76, is sufficient to discourage previously taken samples from slipping distally. Yet, after the device has been removed from the body, the samples can be removed without damage by pulling them distally over the gradually contoured surfaces.

Figure 6:
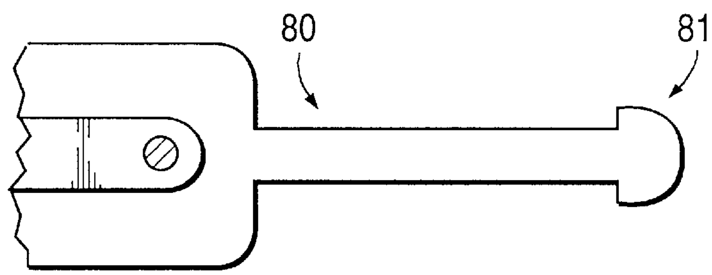

Referring to FIG. 6, a retaining element 80 includes a distal portion 81 having a rounded or spherical shape that atraumatically pierces soft tissue.

Figure 7:
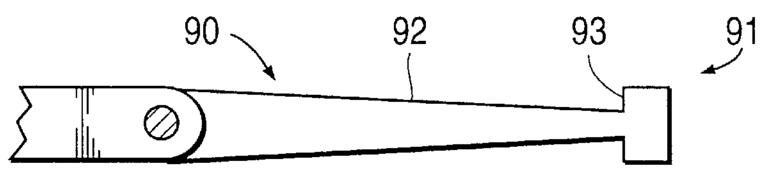

Referring to FIG. 7, an element 90 includes a distal portion 91 having a block-form shape. The body 92 has a gradual slope to smaller diameter in the distal direction causing a ledge 93 that retains samples from sliding proximally.

Figure 8:
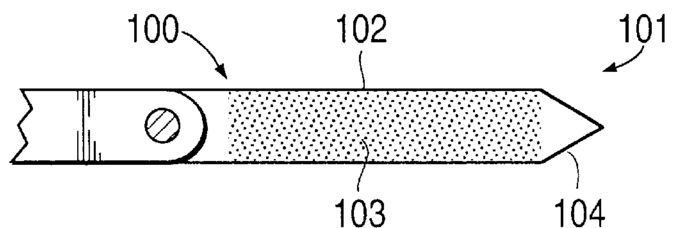

Referring to FIG. 8, in another embodiment, a member 100 has a distal portion 101 with a diameter no greater than a body portion 102. The surface of element includes a texture 103 formed, e.g. by sandblasting, for increasing frictional force between the surface and stored samples. The distal portion 101 includes a sharpened tip 104 and is (optionally) not textured to improve piercing of tissue. Further embodiments do not include a textured surface or a retaining protrusion. The distal portions have a diameter substantially equal to the bodies. The length and diameter of the bodies is selected such that sufficient frictional force exists between the body and the sample to discourage the sample from slipping off distally when the jaws are opened to take an additional sample. Yet, the dimensions of the body are not so large as to detrimentally reduce the sample size.

In various embodiments, the cross-sectional shape of the retaining member is preferably round, but may be of other, preferably symmetric, geometrical configurations, e.g. square, etc. Long, narrow retaining members have the advantage that relatively large samples can be taken, e.g., when not used in a multiple biopsy mode. Other embodiments employ features discussed in "Multiple Biopsy Sampling Device" by Bruce H. Diamond, Donald E. Robinson, Alyssa J. Dassa and Charles Warich, filed Sep. 20, 1993, the entire contents of which is hereby incorporated by reference. The general structure of a typical forceps device is discussed in Bales et al. U.S. Pat. No. 5,133,727, which is also hereby incorporated by reference. A biopsy forceps device that could be modified by the addition of retaining members taught herein is available Radial Jaw™ from Boston Scientific Corporation, Watertown, Mass.

Still further embodiments are in the following claims.

what is claimed is:

1. A device for obtaining tissue samples from a site within a body, said device constructed for severing and storing multiple samples without withdrawing said device from the body, said device having a flexible proximal portion constructed to follow a nonlinear path to said site and a distal portion constructed with a jaw arrangement that can be opened and closed to sever a tissue sample, said device comprising:

an elongated multiple sampling element in the space encompassed by said jaw arrangement, said sampling element having a length, and said element including a distal end portion with a tissue-piercing profile and a proximal end fixed to the distal portion of said device to maintain said element in an orientation extending generally distally to facilitate tissue piercing as said device is urged toward a tissue surface, a retaining protrusion between said proximal end and said distal end portion of said multiple sampling element having a diameter greater than a diameter of a portion of said multiple sampling element for preventing stored sample on said portion of said element proximal of said retaining protrusion from moving distally when said jaw arrangement is opened to sever a successive sample from said surface, and a storage section located proximally of said protrusion and having a length adapted to store multiple samples impaled upon said element, said length of said storage section being a majority of said length of said sampling element, and a majority of said length of said storage section being located proximally of said protrusion.

2. The instrument of claim 1 wherein said sample retaining element is an elongated spear-form member including a single retaining element positioned distal of said storage section and proximally adjacent said tissue piercing profile.

3. The device of claim 2 wherein said storage portion has a first length and said protrusion has a second length less than about 15% of said first length.

4. The device of claim 3 wherein said protrusion and tissue piercing profile are about 5 to 15% of the length of said member proximal of said protrusion.

5. The device of claim 1 wherein the length of said storage section is at least 0.065 inch.

6. The device of claim 5 wherein the length of said storage section is about 0.300 inch.

7. The device of any one of claims 1, 2, 3 or 6 wherein said diameter of said retaining protrusion is about 25–250% larger than a diameter of said storage section immediately proximal of said protrusion.

8. The device of any one of claims 1, 2, 3 or 6 wherein a diameter of said storage section is substantially constant.

9. The device of claim 8 wherein said substantially constant diameter of said storage space is at least 0.010 inch.

10. The device of claim 2 wherein said protrusion and said tissue piercing profile form an arrow head-type profile.

11. The device of claim 1 or 2 wherein said sampling element is constructed for detachment from said device at a location proximal of said storage section.

12. The device of claim 11 wherein said sampling element and device include mating structure so a sampling element can be detached and attached to said device.

13. The device of claim 12 wherein said sampling element and device include a plug and socket-type mating arrangement.

14. The device of claim 1 wherein said distal portion, including said sampling element and jaw arrangement, is constructed for retaining at least five successive samples.

15. The device of claim 1 wherein said sampling element includes textured surface on at least part of its length to facilitate retaining said samples.

16. The device of claim 1 including a gradual, proximal transition region on said retaining protrusion to facilitate distal sliding release of said samples after removal of the device from the body.

17. A device for obtaining tissue samples having a distal end constructed with a jaw arrangement that can be opened and closed to sever said sample, including tissue specimens, polyps and the like, from a surface, comprising:

said device constructed for severing and storing multiple samples, including:

an elongated multiple sampling element in the form of an elongated spear-form member in the space encompassed by said jaws, said member fixed to maintain an orientation extending along a selected length to a distal end to pierce said samples and allow proximal sliding of previous samples along its length during piercing of tissue to take a successive sample, said element including near its distal end a retaining protrusion with diameter greater than the diameter of portions proximal of said protrusion, said protrusion providing sufficient frictional force to substantially retain a sample positioned at least in part proximally of said protrusion from moving distally from said space encompassed by said jaws when said jaws are opened to sever a successive sample from said surface, the length of said protrusion being less than about 15% of the length of said element.

18. The device of claim 17 wherein said retaining protrusion is formed integrally with a tissue-piercing profile having a profile of smaller diameters distal of said retaining protrusion to facilitate piercing of said tissue.

19. The device of claim 18 wherein said element has a length of about 0.300 inch proximal of said retaining protrusion.

20. The device of claim 19 wherein the protrusion and tissue piercing profile are about 5 to 15% of the length of said member proximal of said protrusion.

21. The device of claim 20 wherein the diameter of said retaining protrusion is about 25–50% larger than the diameter of portions of said element proximal of said protrusion.

22. The device of claim 21 wherein said element has a substantially constant diameter proximal of said protrusion.

23. The device of claim 22 wherein said element has a diameter of about 0.010 inch to 0.035 inch proximal of said protrusion.

24. The device of claim 17 including a proximal portion constructed to follow a long torturous path to said site.

25. A method of taking multiple biopsy samples, comprising:

(a) providing a device as described in claim 1, (b) delivering said device deep into the body along a torturous path to a desired site, (c) opening said jaw arrangement, (d) extending said device distally to imbed said spear-form element into a tissue surface at said desired site, (e) closing said jaws to sever a sample from said surface, (f) repeating steps (c)–(e) to take additional samples without removing said device from the body, (g) removing said device from the body, and (h) removing said samples.

26. The method of claim 25 further including:

recovering said samples by detaching said spear-form element from said device.

27. The method of claim 26 including:

repeating steps (c)–(e) to take at least five samples.

28. A device for obtaining tissue samples from a site within a body, said device constructed for severing and storing multiple samples without withdrawing said device from the body, said device having a flexible proximal portion constructed to follow a nonlinear path to said site and a distal portion constructed with a jaw arrangement that can be opened and closed to sever a tissue sample, said device comprising:

an elongated multiple sampling element in the space encompassed by said jaw arrangement, said sampling element having a length and said sampling element fixed to maintain an orientation extending generally distally along a selected length to a distal end to facilitate tissue-piercing as said device is urged toward a tissue surface, said multiple sampling element including a high-friction textured surface to substantially retain said samples from moving distally when said jaw arrangement is opened to sever a successive sample from said surface, and a storage section having a length adapted to store multiple samples impaled on said element, said length of said storage section being a majority of said length of said sampling element, and a majority of said length of said storage section being located proximally of at least a part of said element including said textured surface.

29. The device of claim 28 wherein said element has substantially constant diameter for most of its length.

30. The device of claim 29 wherein said element includes a distal portion which tapers to a sharpened distal end.

31. The device of claim 30 wherein said distal portion has a smooth surface.

32. The device of claim 28 wherein said high friction textured surface is a sand-blasted surface.

33. The device of claim 28 or 32 wherein said textured surface extends substantially on the entire length of said element where said samples are stored.

* * * * *